United States Patent [19]

Brennan

[11] Patent Number: 5,022,389
[45] Date of Patent: Jun. 11, 1991

[54] NASAL SPLINT DEVICE

[75] Inventor: Louis G. Brennan, Stockton, Calif.

[73] Assignee: Cornucopia Medical Products, Inc., Stockton, Calif.

[21] Appl. No.: 528,823

[22] Filed: May 25, 1990

[51] Int. Cl.$^5$ .................. A61F 5/00; A61F 5/04; A61F 9/00

[52] U.S. Cl. .................. 128/76 C; 128/89 R; 128/858

[58] Field of Search .......... 128/857, 858, 163, 89 R, 128/76 C, 89 A, 155

[56] References Cited

U.S. PATENT DOCUMENTS

| | | | |
|---|---|---|---|
| 1,850,016 | 3/1932 | Leduc | 128/857 |
| 3,426,751 | 2/1969 | Radewan | 128/76 C |
| 3,594,813 | 7/1971 | Sanderson | 128/858 |
| 4,153,051 | 5/1979 | Shippert | 128/89 R |
| 4,213,452 | 7/1980 | Shippert | 128/89 R |
| 4,274,402 | 6/1981 | Shippert | 128/89 R |
| 4,340,040 | 7/1982 | Straith | 128/76 C |
| 4,534,342 | 8/1985 | Paxa | 128/89 R |
| 4,901,714 | 2/1990 | Jensen | 128/858 |

*Primary Examiner*—Robert A. Hafer
*Assistant Examiner*—Michael Brown

[57] ABSTRACT

A nasal splint device for retaining a traumatized nose after surgery or injury, and method of applying the nasal splint. A flexible inner splint portion adapted for direct application to nasal skin includes a planar sheet of semi-rigid polymer material having opposing lateral portions and a central bridge portion defined by a pair of substantially parallel outer surface grooves for articulation of the inner splint portion and having elongated cutouts defining a lower dorsal portion of the central bridge portion and lateral portions. A compressible polymeric foam inner layer is attached to the inner sheet material and coextensive with the lateral portions and bridge portion, with a pair of inner foam recesses substantially coextensive with the parallel outer surface grooves. A tacky layer of medical-grade adhesive overlies the inner surface of the foam for direct application to the nasal skin. The flexible inner splint portion, foam layer and tacky adhesive layer form an integral splint member adaptable to individual nasal application by trimming to fit. A compound splint is formed by joining the inner splint portion with a splint stabilizer member includes a thin sheet of malleable metal with a matching stabilizer bridge portion and lateral wing portions forming a T-shape. The stabilizer bridge portion is sufficiently large to overlie a major part of the lower dorsal portion of the lower dorsal portion of the central bridge portion of the integral splint member. Adhesive or another attachment source is provided for attaching the stabilizer bridge portion adjacent the lateral wing portions of the splint stabilizer member to the inner splint portion between the outer grooves along the central bridge portion.

21 Claims, 1 Drawing Sheet

NASAL SPLINT DEVICE

BACKGROUND OF THE INVENTION

This invention relates to splint devices adapted for use during healing of the human nose. In particular, it relates to a novel compound nasal splint or surgical brace device useful for retaining a traumatized nose after surgery or injury.

Treatment of trauma or cosmetic corrective surgery are commonly employed medical procedures. Following surgical correction of external nasal deformities, there is a need to stabilize the external nasal framework until adequate healing has taken place. During the healing period a desired size and shape should be maintained to control edema and to assure symmetry of the healed proboscis member. Numerous attempts have been made to provide suitable casts, adhesive bandages and nasal splints for the purpose of maintaining immobility of bony segments following surgery. Many of these are difficult to fabricate, to apply to the traumatized area or to retain in position. Presently available nasal splints include the Conco "Alumafoam" product, which comprises a malleable metal outer sheath lined with resilient foam. Other splint devices are described by Shippert in U.S. Pat. Nos. 4,153,051; 4,313,452; and 4,274,402; incorporated by reference. The "Denver Splint" is a compound device requiring careful application of a series of adhesive strips as a base layer, a dorsum center pad, an intermediate Velcro loop segment layer, and a formed outer restraining member attached by opposing Velcro hook means.

It is an object of the present invention to provide an articulated nasal splint with simple one-step application. It is another object to permit direct application of a splint to nasal skin without preliminary taping. A further object is to provide essentially uniform pressure to the traumatized nose, with symmetrical nasal compression and shaping forces with controlled, variable narrowing of the nose. Another object is to provide a comfortable device with cushioned, light-weight materials and resilient design, allowing for expansion/contraction with nasal edema or swelling.

SUMMARY OF THE INVENTION

A novel compound post-operative nasal splint has been devised comprising: a first flexible integral inner splint member adapted for direct application to nasal skin, including a thin, resilient polymer sheet having opposing lateral portions and a central bridge portion defined by a pair of spaced bendable hinge lines permitting articulation of the inner splint portion and having elongated cutouts defining a lower dorsal portion of the central bridge portion and lateral portions; a compressible polymeric foam inner layer bonded to the resilient sheet extending under the lateral portions and bridge portion and being recessed toward the resilient sheet opposite said hinge lines, thereby preventing bunching of the foam layer during articulation; and a tacky layer of medical-grade pressure adhesive applied to said foam layer for direct application to the nasal skin following removal of temporary protective stripping; said flexible inner splint member being shearable for trimming to fit.

The compound splint also comprises a separate second splint stabilizer member comprising a thin sheet of malleable metal for manual molding in situ over the inner splint member, said outer splint stabilizer having a preformed stabilizer bridge portion sufficiently large to overlie a major part of the lower dorsal portion of the central bridge portion of the integral splint member and having lateral wing portions. The stabilizer may be attached to the inner splint portion by various means, preferably joining the compound splint before application to the nose. In one embodiment the entire stabilizer bridge portion adjacent the lateral wing portions is provided with adhesive means for attaching the splint stabilizer member between the hinge lines to the central bridge portion following nasal application of the flexible inner splint portion.

These and other objects and features of the invention will be seen from the following description and in the drawing.

BRIEF DESCRIPTION OF THE DRAWING

FIG. 1 two-part is a top edge view of two separated splint members wherein

DESCRIPTION OF PREFERRED EMBODIMENTS

In the following description, primary emphasis is placed on surgical correction of external nasal deformities, as in cosmetic plastic surgery.

Figure 1A:
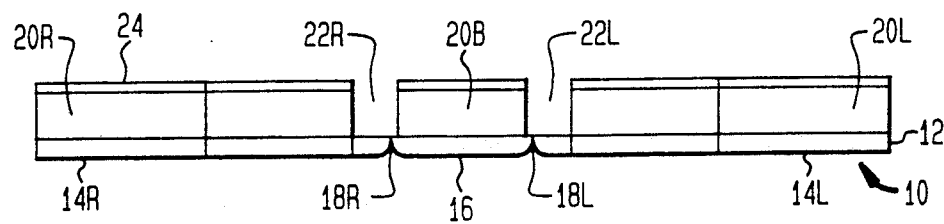
FIG. 1A depicts the flexible planar sheet composite in its initial flattened position prior to deformation during use.
Figure 1B:
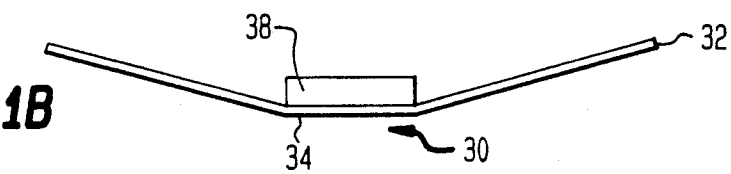
FIG. 1B depicts the thin metal splint stabilizer member. Layer thicknesses are exaggerated for clarity.
Figure 2:
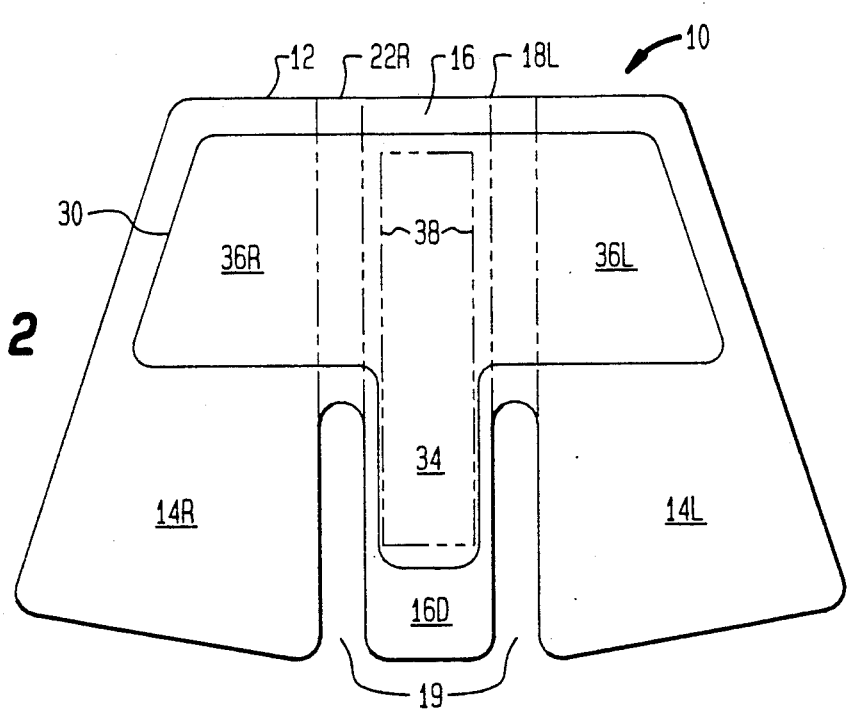
FIG. 2 is a front elevation view of the two splint members, showing their overlying relationship according to the present invention.

In FIGS. 1A, 1B and 2, the nasal splint device is shown in its production form prior to articulation or bending of the first composite splint member 10 for retaining a traumatized nose after surgery or injury. The flexible inner splint portion 10 includes a planar sheet main structural component 12 of semi-rigid polymer material having opposing lateral portions 14R, 14L and a central bridge portion 16 defined by a pair of substantially parallel outer surface grooves 18R, 18L for articulation. The inner splint portion also has elongated cutouts 19 defining a lower dorsal portion 16D of the central bridge portion and lateral portions 14. A compressible polymeric foam inner layer 20 is bonded or otherwise suitably attached to the inner planar sheet 1 and coextensive with the lateral portions and bridge portion, with a pair of inner foam recesses 22R, 22L substantially coextensive with the outer grooves 18R, 18L. A tacky layer 24 of medical-grade adhesive is applied overlying the inner surface of the foam sections 20B, 20R, 20L for direct application to the nasal skin. The flexible inner splint portion, foam layer and tacky adhesive layer forming an integral splint member adaptable to individual nasal application by trimming to fit the individual patient. The composite member 10 can be supplied with stripping paper or other non-adherent layer (not shown) for articulation of the first splint composite member over the post-surgical nose before removing the stripping layer for direct application to nasal skin, in a manner to be described.

The splint stabilizer second member 30 comprises a thin sheet 32 of malleable metal with a matching stabilizer bridge portion 34 and lateral wing portions 36R, 36L forming a T-shape, wherein the stabilizer bridge dorsal extension portion 34 is sufficiently large to overlie a major part of the distal dorsal strut or lower portion 16D of the central bridge 16 of the integral splint member 10. In order to attach the second splint stabilizer member to form the compound splint, at least the upper stabilizer bridge portion 34A adjacent the lateral wing portions 36 has a patch of foam padded tacky adhesive 38 for attachment to the splint stabilizer member 10 between the outer grooves along at least an upper part of the central bridge portion 16 after articulation of the flexible inner splint portion during application. In order to assure adequate adhesion during use, the adhesive may be applied along the entire length of the splint stabilizer bridge portion, either by initial bonding to the splint stabilizer or to the inner splint surface opposite the point of attachment. The particular means for attaching the stabilizer unit 30 to the inner splint unit 10 is not a critical aspect of the invention. For instance, a quick-setting cement can be used, alone or in combination with other fasteners or adhesives. It is preferred to preassemble the compound splint members by firmly adhering the stabilizer member to the inner splint bridge prior to application of the compound assembly to the nose. The compound splint can be readily removed without patient discomfort. This is achieved by employing solvent-softenable medical grade adhesive. Foam adhesive attachment unit 38 permits a secure, water resistant seal during the healing period; however, the surgeon can daub a small amount of acetone or the like onto the interior adhesive 38 to remove the compound splint stepwise.

The nasal splint device is preferably configured with the splint stabilizer member lateral wing portions 36R, 36L extending laterally from the upper bridge portion of the nose toward side edges of the inner splint portion to provide essentially uniform pressure across areas 14R, 14L over the post-surgical nose with symmetrical nasal compression being thereby obtained. The inner splint member may have a substantially trapezoidal peripheral shape. Preferably, the semi-rigid polymer material of the inner splint portion is formed of a thermoplastic inert polymer having sufficient elasticity to permit controlled expansion and contraction for nasal edema or swelling.

The compressible polymeric foam inner layer comprises soft closed cell "Volara" polyethylene having a thickness of about 1-4 mm (e.g., 1/16-⅛ inch). The preferred material for the malleable metal is a thin annealed aluminum sheet (e.g., 0.5mm thick type 6061-TO). The tacky layer usually consists essentially of dermatologically acceptable adhesive and is protected by peelable temporary stripping material during shipment and pre-application articulation.

A representative splint size has the following typical approximate dimensions relative to a cephalad (top splint edge) length of about 30 millimeters: Inner splint trapazoidal periphery—about 150 mm; bridge width—8 mm; top and side edges—32 mm; cutouts—15×3 mm; flare angle 15-20 degrees each side; splint stabilizer top edge—28 mm; wing height—15 mm; dorsal strut length—12 mm; bridge width—9mm; overall width—38 mm; foam/adhesive attachment pad—8×12 mm. These relative dimensions provide for the dorsal strut extending over a major part of the underlying portion of the inner splint, while permiting the dorsal extremity to extend caudally for enhancing supratip depression of the nose.

Figure 3:
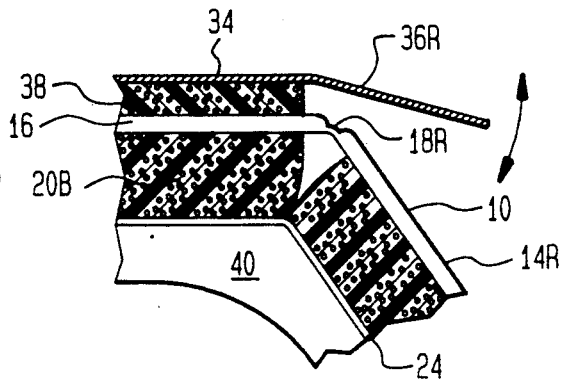
FIG. 3 is a segmented horizontal cross-sectional view showing the compound splint application to a human nose.

FIG. 3 is an enlarged view of the compound splint in the depicting one-step application of a pre-assembled splint to a post-surgical nose 40. Inner splint bridge portion 20B is pressed onto the front of the nose 40 and held by adhesive layer 24. The bridge portions of the splint 16, 34 are joined by adhesive foam layer 38, extending along substantially the entire length of bridge member 34. The inner splint later portion 14R is bent along recessed hinge line 18R, and pressed inwardly to adhere the lateral foam layer to the nasal skin via adhesive 24. After fixing the resilient inner splint member in place on the nose, the lateral wing member 36R and other portions of malleable metal sheet member 34 are pressed inwardly, as indicated by the reversible arrow to provide a splint stabilizing force against the resilient inner splint member 12. This bending action can be reversed during post-healing removal of the compound splint to retract the metal wings from the inner splint for manipulation thereof.

The surgical method for treating a post-surgical or traumatized human nose by application of a post-operative nasal splint includes the sequential steps of: a) expressing edema from the traumatized nose and cleaning the nasal skin preparatory to receiving direct adhesive contact; b) trim fitting and manually molding the flexible integral inner splint member, optionally before or after the surgical procedure, as described; c) attaching the splint stabilizer member over the inner splint member, whereby the splint stabilizer overlies a major part of the lower dorsal portion of the lower dorsal portion of the central bridge portion of the integral splint member; d) exposing a tacky layer of medical grade pressure adhesive applied to the foam layer; and e) directly applying the flexible integral inner splint member to the nasal skin following removal of temporary protective stripping, with initial contact being made with the dorsal aspect of the nose and the composite inner splint then being folded over the sides of the nose. The above sequence can be altered to join the stabilizer to the inner splint member after separate application of the inner splint member. Usually, the splint stabilizer is compressively molded manually to conform to the inner splint surface by pinching and bending the malleable metal to obtain the desired degree of narrowing and controlled nasal width. The distal dorsal strut portion 16D of the inner splint can be displaced inwardly by bending the partially overlying lower (caudal) portion 34 of the stabilizer, resulting in a spring-like action which assists in modeling the supratip region of the nose during healing.

The invention has a number of advantages and features which can be realized by employing a relatively few basic manufactured sizes which can be trimmed to fit children and adult nasal structures of different size ranges. The device accommodates various nasal shapes, due to its articulated design. By employing the composite inner splint, a simple one-step application follows a trial fitting (with adhesive protected by the pull-off layer) and trimming with ordinary surgical scissors. The flat inner splint design permits custom "tailoring" of the plastic composite and provides a wide range of adaptability of a single size. Direct application of the inner splint member to nasal skin using medical grade tacky adhesive eliminates preliminary taping of the nose.

It is understood that the application techniques can be employed with strips of medical grade adhesive tape (e.g.—"Steri-strip") to achieve "fine-tuning" and modeling of the nasal tip. For instance, horizontally strapping a thin piece of adhesive tape across the base or columella of the nose to the side members of lateral portions of the inner splint narrowing to produce a desirable tip effect. This technique elevates the nasal tip against the distal-most (caudal) part of the inner splint member dorsal strut. The elasticity of the lateral portions of the inner splint member further enhances the ability of the lower, inferior (or more caudal) aspect of the nose to expand by swelling, with greatly diminished incidence of pressure damage to the skin during healing.

The skilled plastic surgeon will appreciate that the tri-sectional foam-lined inner splint with recessed foam at the lateral bridge creases or hinge lines will prevent "bunching" of the foam layer adjacent the skin (as depicted in FIG. 3), thus preventing wrinkling of the skin during the healing process. The device diminishes skin damage, since elasticity of the polymeric sheet component allows for expansion with nasal edema or swelling, and subsequent contraction as the swelling subsides. The results in essentially uniform pressure being applied to the nose, which distributes and accommodates swelling effects. As opposed to prior malleable splint devices, the new compound splint has predetermined bridge fold lines, whereby articulation during the surgical procedure is maintained within the configuration of the prefolded starting shape. This is achieved in the manufacturing process by forming the metal stabilizer member at the desired crease lines to facilitate the manual molding process during attachment of the splint stabilizer to the inner composite. This feature provides symmetrical nasal compression and shaping.

During the post-operative healing period patient comfort is assured by light weight and cushioning of the device. The relatively thin compound splint can be worn with eyeglasses, since the splint is designed to accept an ordinary eyeglass frame unobtrusively. Other desirable features include flesh-colored or decorative materials of construction or coatings, with the entire compound splint being manufactured of water-resistant materials.

Ease of removal of the compound splint will be appreciated by the skilled practitioner. Localized central attachment of the stabilizer over the bridge permits the malleable metal material to be straightened outwardly by unbending the stabilizer member to an open spread position, thus relieving pressure on the inner splint member. This procedure permits insertion of an absorbent applicator tip soaked with adhesive remover/solvent (if needed) beneath the gently lifted edge of the inner splint member, thus freeing it from the nasal skin. Reduced discomfort during removal is assured in addition to maximum skin protection during healing.

Materials and methods of manufacture for the present invention are varied. Polyesters, polyolefins, polyamides and other resins have mechanical properties suitable for use as the main structural component. Polyalkylene phthalic ester synthetic resins, such as polyethylene terephthalate (PET) or polybutylene terephthalate (PBT) are commercially available with an elastic modulus and orientation properties which can provide a "living hinge" effect at the bending point of the bridge grooves. The preferred PBT polymeric materials are commercially available as alloys or blends with other synthetic resins, such as elastomers, PET, etc sold under the designations "Celanex 5330, Valox, Arlon 101, Ultradur, Rynite", etc. Copolymers and blends with polycarbonates, urethanes, nylons, polyethers, acrylics, ABS are within the skill of the art in selection of suitable materials. Impact modifiers, fibrous reinforcement, fillers, colorants and biocides are possible resin additives. The desired fatigue resistance, dimensional stability and water resistance properties of the resin system can be chosen according to known parameters. Material handling, molding, adhesive bonding, machining and embossing techniques are described in Modern Plastics Encyclopedia (1986-87),pp.6-111. The preferred PBT blends have a tensile strength of at least 10,000 psi and melt point of about 400F.

Thermoplastic sheet (i.e. about 1-4 mm thickness) can be laminated with adhesive-coated foam and the individual composite inner splint member die-cut from a larger uniform composite sheet material. The preferred synthetic polymer sheet of the inner splint member comprises thermoplastic polybutylene terephthalate resin obtained as a preformed sheet having a uniform thickness of about 0.8mm (0.032 in). Preferred synthetic polymers typically contain about 5 to 95 wt% polybutylene terephthalate resin in alloy resin blend, having a tensile strength of about 4000 20,000 psi, tensile modulus of about 2000-4000 psi, high dynamic fatigue strength, and cold working properties. The bridge grooves can be formed in the thermoplastic sheet surface by mechanical scoring simultaneously with cutting of the splint shape, resulting in a cold working of the polymeric structure to impart desirable "living hinge" properties to the scored portions of the sheet. Alternatively, the hinge lines may be thermally formed, cut or milled into the surface of the composite splint in a separate operation, which can also include the step of removing excess foam material from the opposite side by milling, hydraulic cutting, etc.

Bonding of the composite materials can be effected with various adhesives, such as cyanoacrylate, epoxy, urethane and/or silicone; however, it is advantageous to prefabricate the foam members from double coated sheet protected on both sides by removable protective layers over medical grade tacky adhesive, which can be used not only in contact with the nasal skin but also to adhere the composite materials. A suitable soft foam sheet, such as "Volara 2A/2E" crosslinked polyethylene, may have a normal density of about 2 PCF, compression strength of 5.5 psi (pounds/square inch) at 25% psi, compression set of 16% original thickness, K factor 0.25 and maximum water absorption of 0.004 pounds/cut surface area. Other elastic foams of polyurethane, polypropylene, etc., may be used as desired.

It is desirable to preshape the stabilizer unit shown in FIG. 1B by forming a slight (ie −15 degree) angle to facilitate manipulation of the compound splint during application. The foam bridge and lateral portions can also be precut and later bonded to a precut and formed main inner splint component.

I claim:
1. A nasal splint device for retaining a traumatized nose after surgery or injury comprising:
   a flexible inner splint portion adapted for direct application to nasal skin, including a planar sheet of semi-rigid polymer material having opposing lateral portions and a central bridge portion defined by a pair of substantially parallel outer surface grooves for articulation of the inner splint portion and having elongated cutouts defining a lower dorsal portion of the central bridge portion and lateral portions;

a compressible polymeric foam inner layer attached to the inner planar sheet material and coextensive with the lateral portions and bridge portion, with a pair of inner foam recesses substantially coextensive with the parallel outer surface grooves;

a tacky layer of medical-grade adhesive overlying the inner surface of the foam for direct application to the nasal skin; said flexible inner splint portion, foam layer and tacky adhesive layer forming an integral splint member adaptable to individual nasal application by trimming to fit;

a splint stabilizer member comprising a thin sheet of malleable metal with a matching stabilizer bridge portion and lateral wing portions forming a T-shape, wherein the stabilizer bridge portion is sufficiently large to overlie a major part of the lower dorsal portion of the lower dorsal portion of the central bridge portion of the integral splint member;

adhesive means for attaching the stabilizer bridge portion adjacent the lateral wing portions of the splint stabilizer member to the inner splint portion between the outer grooves along the central bridge portion, thereby permitting articulation of the flexible inner splint portion during application.

2. The nasal splint device of claim 1 wherein the splint stabilizer member lateral wing portions extend laterally from the upper bridge portion of the nose toward side edges of the inner splint portion to provide essentially uniform pressure to a traumatized nose with symmetrical nasal compression.

3. The nasal splint device of claim 1 wherein the semi-rigid polymer material of the inner splint portion is formed of a thermoplastic inert polymer having sufficient elasticity to permit controlled expansion and contraction of nasal edema or swelling; wherein the compressible polymeric foam inner layer comprises soft closed cell polyethylene; and wherein the malleable metal comprises annealed aluminum.

4. The nasal splint device of claim 1 wherein the tacky layer consists essentially of dermatologically acceptable adhesive and wherein the tacky layer is protected by peelable temporary stripping material.

5. A compound post-operative nasal splint comprising:

a flexible integral inner splint member adapted for direct application to nasal skin, including a thin, resilient synthetic polymer sheet having opposing lateral portions and a central bridge portion defined by a pair of spaced bendable hinge lines permitting articulation of the inner splint portion and having elongated cutouts defining a lower dorsal portion of the central bridge portion and lateral portions;

a compressible polymeric foam inner layer bonded to the resilient sheet extending under the lateral portions and bridge portion and being recessed toward the resilient sheet opposite said hinge lines thereby preventing bunching of the foam layer or wrinkling of nasal skin during articulation;

a tacky layer of medical-grade pressure adhesive applied to said foam layer for direct application to the nasal skin following removal of temporary protective stripping; said flexible inner splint member being shearable for trimming to fit;

a separate splint stabilizer member comprising a thin sheet of malleable metal for manual molding in situ over the inner splint member, said splint stabilizer having a preformed stabilizer bridge portion sufficiently large to overlie a major part of the lower dorsal portion of the central bridge portion of the integral splint member and having lateral wing portions; and means for attaching the splint stabilizer member along the stabilizer bridge portion adjacent the lateral wing portions thereof to the integral splint member between the hinge lines at the central bridge portion thereof following nasal application of the flexible inner splint portion.

6. The nasal splint of claim 5 wherein the splint stabilizer member lateral wing portions extend partially from the upper bridge portion of the nose toward side edges of the inner splint member and overlying central portions of the inner splint member to provide controlled pressure and symmetrical nasal compression.

7. The nasal splint of claim 6 wherein the inner splint portion is formed of semi-rigid, inert, thermoplastic polymer material having sufficient elasticity to permit controlled expansion and contraction of nasal edema during swelling; wherein the compressible polymeric foam inner layer comprises soft closed cell polymer; and wherein the malleable metal comprises annealed aluminum 8. The nasal splint of claim 5 wherein the inner splint member has a substantially trapezoidal peripheral shape.

9. The nasal splint of claim 5 wherein the synthetic polymer sheet of the inner splint member comprises thermoplatic polybutylene terephthalate resin.

10. The nasal splint of claim 9 wherein the synthetic polymer sheet contains about 5 to 95 wt% polybutylene terephthalate resin in alloy resin blend, having a tensile strength of about 4000-20,000 psi, tensile modulus of about 2000-4000 psi, high dynamic fatigue strength, and cold working properties.

11. A method for treating a traumatized human nose by application of a post-operative nasal splint comprising the steps of: a) expressing edema from the traumatized nose and cleaning the nasal skin preparatory to receiving direct adhesive contact; b) manually molding a flexible integral inner splint member including a thin, resilient thermoplastic sheet having opposing lateral portions and a central bridge portion defined by a pair of spaced bendable hinge lines permitting articulation of the inner splint portion and having elongated cutouts defining a lower dorsal portion of the central bridge portion and lateral portions, a compressible polymeric foam inner layer bonded to the resilient sheet extending under the lateral portions and bridge portion and being recessed toward the resilient sheet opposite said hinge lines, thereby preventing bunching of the foam layer during articulation; c) attaching a splint stabilizer member comprising a thin sheet of malleable metal over the inner splint member, said splint stabilizer having a preformed stabilizer bridge portion sufficiently large to overlie a major part of the lower dorsal portion of the central bridge portion of the integral splint member and having lateral wing portions; d) exposing a tacky layer of medical-grade pressure adhesive applied to said foam layer; and e) directly applying the flexible integral inner splint member to the nasal skin following removal of temporary protective stripping.

12. The method of claim 11 wherein the stabilizer bridge portion adjacent the lateral wing portions has a layer of adhesive for attaching the splint stabilizer member between the hinge lines at a central bridge portion following nasal application of the flexible inner splint portion, and wherein the flexible inner splint member is trimmed to fit the traumatized nose.

13. The method of claim 12 wherein the inner splint member is prefitted to the individual nose prior to adhesion by placing said inner splint member on the nose and manually forming same prior to removing the temporary protective stripping therefrom.

14. The method of claim 11 including the step of taping over lateral wing portions of the splint and nose to provide controlled modeling of the nasal tip.

15. The method of claim 11 including the step of applying surgical tape horizontally across the columella of the nose to lateral portions of the splint to provide controlled modeling of the nasal tip.

16. The method of claim 11 herein the stabilizer member is attached to the inner splint member prior to adhering the compound splint to the nasal skin.

17. A post-surgical procedure for treating a human nose by application of a compound nasal splint including the sequential steps of:

preparing the post-surgical nose for receiving direct adhesive contact by expressing edema from the nose and cleaning the nasal skin;

fitting to the prepared nose a flexible integral inner splint member; said inner splint member including a thin resilient polymer sheet having opposing lateral portions and a central bridge portion defined by a pair of spaced bendable hinge lines permitting articulation of the inner splint portion and having elongated cutouts defining a lower dorsal portion of the central bridge portion and lateral portions, a compressible polymeric foam inner layer bonded to the resilient sheet extending under the lateral portions and bridge portion and being recessed toward the resilient sheet opposite said hinge lines, thereby preventing bunching of the foam layer during articulation;

said inner splint member having attached thereto a splint stabilizer member; said splint stabilizer member comprising a thin sheet of malleable metal over the inner splint member and having a preformed stabilizer bridge portion sufficiently large to overlie a major part of the lower dorsal portion of the central bridge portion of the integral splint member and having lateral wing portions;

exposing a tacky layer of medical-grade pressure adhesive applied to said foam layer of the inner splint member;

directly applying the flexible integral inner splint member to the nasal skin;

molding the splint stabilizer member by pressing the malleable metal sheet in compressive relation to the inner splint member.

18. The procedure of claim 17 wherein individualized narrowing of portions of the nose width is achieved by variable compression with pinch molding of the splint stabilizer member.

19. The procedure of claim 18 wherein symmetrical nasal compression is applied in predetermined portions of the nose by the resilient polymer material, cutouts and bendable hinges of the inner splint member.

20. The procedure of claim 17 wherein individualized shaping of the nasal tip is achieved by localized compression of the splint stabilizer member on the nasal dorsum in the supratip region thereof.

21. The procedure of claim 17 including the step of applying surgical tape horizontally across the columella of the nose to lateral portions of the splint to provide controlled modeling of the nasal tip, and depressing the lower dorsal portion of the inner splint member inwardly by compressively shaping the splint stabilizer member overlying the desired depressed portion of the dorsum.

* * * * *